United States Patent [19]

Sinko et al.

[11] Patent Number: 5,279,590
[45] Date of Patent: Jan. 18, 1994

[54] CATHETER PLACEMENT APPARATUS

[75] Inventors: George E. Sinko; Charles A. Jones; H. Douglas Courtney, all of San Antonio, Tex.

[73] Assignee: Gesco International, Inc., San Antonio, Tex.

[21] Appl. No.: 934,168

[22] Filed: Aug. 21, 1992

[51] Int. Cl.$^5$ .............................................. A61M 5/00
[52] U.S. Cl. ................... 604/263; 604/110; 604/198; 604/162
[58] Field of Search ............... 604/164, 168, 165, 138, 604/110, 162, 33, 197, 198, 236; 128/657, 658

[56] References Cited

U.S. PATENT DOCUMENTS

| | | |
|---|---|---|
| 3,463,152 | 8/1969 | Sorenson . |
| 3,536,073 | 10/1970 | Farb . |
| 4,108,175 | 8/1978 | Orton . |
| 4,160,450 | 7/1979 | Doherty . |
| 4,306,562 | 12/1981 | Osborne . |
| 4,664,653 | 5/1987 | Sagstetter et al. . |
| 4,664,654 | 5/1987 | Strauss ............... 604/198 |
| 4,676,783 | 6/1987 | Jagger et al. . |
| 4,702,738 | 10/1987 | Spencer . |
| 4,723,942 | 2/1988 | Scott ............... 604/164 |
| 4,747,831 | 5/1988 | Kulli . |
| 4,747,836 | 5/1988 | Luther ............... 604/198 |
| 4,781,692 | 11/1988 | Jagger et al. . |
| 4,832,696 | 5/1989 | Luther et al. . |
| 4,865,592 | 9/1989 | Rycroft ............... 604/197 |
| 4,950,252 | 8/1990 | Luther et al. . |
| 5,000,740 | 3/1991 | Ducharme et al. ............... 604/162 |
| 5,120,311 | 9/1992 | Sagstetter et al. ............... 604/110 |
| 5,137,521 | 8/1992 | Wilkins ............... 604/198 |

*Primary Examiner*—C. Fred Rosenbaum
*Assistant Examiner*—V. Alexander

[57] ABSTRACT

Apparatus for introducing a catheter into a patient's vein comprises a tubular housing having an axially extending guide slot extending from a point adjacent the forward end of the housing to a point adjacent the rear end of the housing. A tubular transparent mount for a hollow hypodermic needle is slidably mounted in the tubular housing with the sharpened end of the needle projecting forwardly. The overall length of the needle mount and needle is less than the length of the housing. A locking element rotatably mounted on the needle mount projects through the elongated slot and is selectively engaged with recesses provided in the forward and rear end wall portions of the elongated slot, by rotation relative to the needle mount, to lock the needle mount in an operative position with the needle projecting out of the housing, or an inoperative position with the needle retracted into the housing. A short length catheter or an axially splittable introducer sheath may be mounted on the needle in its projecting position for insertion with the needle into the patient's vein. After insertion of either a catheter or a catheter introducer sheath in the patient's vein, the needle is retracted from the vein to its inoperative position in the housing and the exposed opening in the sharpened end of the needle is surrounded and sealed by a mass of elastomeric material mounted in the forward end of the bore of the housing.

10 Claims, 4 Drawing Sheets

CATHETER PLACEMENT APPARATUS

BACKGROUND OF THE INVENTION

1. Field of the Invention

The invention relates to an assemblage for the introduction of a catheter into a vein while protecting the clinician from accidental needle sticks after withdrawal of a sharp needle. The assemblage may be used for regular over the needle catheters made of a stiff material, or with slight modifications, for introducing a long soft catheter thru a peelable introducer sheath.

2. Background of the Invention

A body penetrating needle is probably the most highly used instrument employed by physicians and nurses. The penetration of the body tissue is generally accomplished by a sharpened end of a hollow needle, which normally is inserted through subcutaneous body tissue to penetrate a selected vein lying close to the body surface. Thousands of such needles are employed daily for the injection of medicinal fluids, by having the non-inserted end of the needle connected to a hypodermic syringe. In many cases, however, a continuous controlled flow of fluid into the selected patient vein is desired and the sharpened hollow needle is employed to penetrate the selected vein and effect the introduction of a catheter into such vein. The catheter is in turn connected to an elevated bag of medicinal fluid after the hollow needle is withdrawn from the body and the catheter.

In other cases, it becomes highly desirable to inject the medicine at a vein location closer to the central vasculature for better hemodilution. In such case, a sharpened hollow needle is employed to effect the initial puncture of the selected vein. An axially splittable catheter sheath or introducer is mounted in surrounding relationship to the body of the needle and follows the needle into the selected patient vein. The needle is then withdrawn from the catheter introducer, and a small diameter, flexible catheter is fed through the bore of the catheter introducer into the vein, and then along the vein to a position to which direct application of medication is desired. The catheter sheath is then withdrawn and axially split for removal from the body and the catheter. See, for example, U.S. Pat. No. 4,306,562 to Osborne.

In all such utilization of hollow needles having sharpened ends, there is always the risk that the physician or nurse using the needle may be scratched by the sharpened end of the needle following its withdrawal from the patient's body. The same risk of inadvertent scratching is faced by those medical health personnel who have to dispose of the used needles. The prevention of accidental scratching of any person by a used needle is obviously highly desirable to minimize accidental infection from patients who have HTLV (AIDS) virus, hepatitis or other highly infectious diseases. There is also the risk of inadvertent contact with blood leaking out of the end of the needle when withdrawn from the body.

The problem of safe, yet convenient placement of catheters in a patient's vein or other body organ has been recognized in the prior art. U.S. Pat. No. 4,832,696 to Luther, et al. provides a needle assembly comprising an elongate hollow housing which mounts the needle. A needle guard is slidably mounted within the housing and is adapted to be moved forward along the needle. Following use, the needle and housing are retracted and the needle guard becomes permanently locked with the housing in a position in which it covers the needle.

A similar device is disclosed in U.S. Pat. No. 4,950,252 to Luther, et al. In both of the aforementioned Luther, et al. patents, the needle assembly is primarily designed to permit the insertion of a so-called "over-the-needle" catheter. In other words, a short length, relatively rigid catheter is mounted in surrounding relationship to the hollow needle whose sharpened end projects out of the end of the catheter. The catheter is then inserted into the selected patient vein concurrently with the penetration of the vein by the sharpened end of the hollow needle. When the needle is withdrawn, the catheter remains in position and may be secured to the patient by adhesive tape so that it may be repeatedly used.

Unfortunately, catheters of the type for which the Luther, et al. needles were designed can only be permitted to remain in the patient for a period generally not in excess of 48 to 72 hours. This limitation is probably due to the relatively stiff material the catheter is made of which is required for the over-the-needle catheter in order to permit the sealed attachment thereto of a tube leading to a bag of medicinal fluid.

Another requirement of a catheter placement apparatus is that after the needle and catheter have been presumably inserted into a vein (venipuncture), the proper insertion must be confirmed by a flow of blood from the vein. Hence, it is highly desirable that the needle mounting assemblage include a flash chamber having at least a portion of its walls transparent and being in communication with the outer end of the hollow needle so that the initial flow of blood may be readily observed by the operator of the needle. This problem is discussed in U.S. Pat. No. 4,108,175 to Orton, who also discusses at length the desirability of having a needle operating mechanism that can be controlled entirely by one hand.

U.S. Pat. No. 4,160,450 to Doherty discloses a protective mounting assemblage for a venipuncture needle wherein the needle is secured to a hub which is slidably mounted within a hollow housing. The movements of the needle relative to the housing are produced by movements of a tube projecting axially out of the housing. After venipuncture has been achieved, the tube is pulled outwardly relative to the housing to retract the needle within the housing. This structure obviously cannot be employed for insertion of an elongated catheter into the selected vein. Medication must be supplied through the tubing that is operatively connected to the hub mounting the needle.

U.S. Pat. No. 4,676,783 to Jagger, et al. discloses a needle protective apparatus similar to the Doherty patent.

U.S. Pat. No. 4,664,653 to Sagstetter, et al. discloses a hypodermic syringe wherein the same needle may be repeatedly utilized, a feature contraindicated in clinical IV protocols. The needle is pushed forward relative to a housing by a plunger element to penetrate a bellows-type covering element and move into puncturing engagement with the skin of the patient. Following the injection of medication, pulling back the plunger will retract the needle into the interior of the bellows unit which assumes an axially extended cylindrical configuration. Obviously, this construction provides no help in reducing the transmission of infectious diseases by repeated usage of a needle.

U.S. Pat. No. 4,702,738 to Spencer discloses a hypodermic syringe wherein the needle is moved between an operative and an inoperative protected position by axial movement of a plunger mounting the needle relative to a surrounding housing. This structure could not be effectively employed for the insertion of a short catheter or a catheter introducer into the patient's vein.

U.S. Pat. No. 4,747,831 to Kulli discloses a needle operating assemblage which can be utilized for insertion of a cannula or over-the-needle catheter wherein the positioning of the needle in its operative opposition compresses a spring between a shoulder provided on the outer end of the needle and a latch mounted for radial movement relative to the housing. After the venipuncture is accomplished, depressing the latch permits the needle to be retracted by the spring to a position where in the pointed end of the needle lies within the end of the housing.

U.S. Pat. No. 4,664,654 to Strauss also utilizes a compressed spring to return the needle to its protected position within the housing.

U.S. Pat. No. 3,536,073 to Farb discloses an enlarged needle having a bore of sufficient diameter to accommodate a catheter. The needle is secured to a plunger which is slidably mounted within housing. A tubular protective sheath is disposed intermediate the needle and the housing and the protective tubing can be advanced to surround the needle after it is withdrawn from the patient's body. This structure obviously requires that the entire operating apparatus be slidably removed over the entire length of the catheter.

U.S. Pat. No. 3,463,152 to Sorenson discloses a catheter placement unit for inserting a catheter into a patient vein through the lumen or bore of the hollow needle. Once the catheter placement has been made, the needle is retracted and is secured in a retracted position in a housing by a strip of adhesive tape which holds the entire apparatus on the patient's body. This is obviously a highly undesirable feature.

Lastly, U.S. Pat. No. 4,781,692 to Jagger, et al. discloses a protective arrangement for a catheter insertion needle wherein the needle is pulled into a protective position within a surrounding tube by a pulling force applied through a flexible tube.

The foregoing discussion of the prior art indicates that many efforts have been made to provide a simple, economical, yet highly protective mechanism for inserting a catheter of either the short, rigid type or the long, flexible type into a desired location in a patient's vein, nonetheless, there is room for improvement of such devices and such improvements are provided by the present invention.

SUMMARY OF THE INVENTION

This invention provides a catheter intravenous placement apparatus which comprises a tubular main housing having an elongated, axially extending guide slot formed in the wall of the main housing, starting at a location adjacent to the forward end of the main housing and extending toward the rear end of the main housing. A tubular needle mount is slidably mounted in the bore of the main housing and is movable from a first position adjacent the forward end of the main housing to a rearward position adjacent to the rear end of the main housing. A hollow vein piercing needle having one sharpened end, has its other end fixedly mounted in the forward end of the needle mount. The total axial length of the needle and the needle mount is proportioned to be not greater than the axial length of the interior of the main housing so that movement of the needle mount to the rear end of the main housing will dispose the entire length of the needle within the bore of the main housing, hence in a protective position.

A radial projection is provided on the needle mount which is slidably engagable with the elongated guide slot in the main housing to maintain the angular alignment of the needle opening in an upwardly facing relation as the needle mount and needle are shifted from a forward position wherein the needle is projecting out of the housing, to a rearward position where the needle is retracted to lie wholly within the housing. A radial locking tab is mounted on the needle mount for rotational or angular movement relative to the axis of the needle amount, hence relative to the axis of the main housing. The locking tab projects through the guide slot to be conveniently engagable by the fore finger of the person using the apparatus. Recesses are provided in the wall of the guide slot at both its forward and rearward ends to be selectively engaged by the radial locking tab to position the needle and needle mount in an extended operative position for insertion of the needle into the patient's body, or in a rearward position where the needle is entirely disposed within the confines of the main housing and permanently locked into place.

With the above described basic construction, a short tubular catheter may be mounted on the projecting end of the needle and inserted into the patient's vein concurrently with the puncturing of the vein by the needle. Alternatively, a short, axially splittable catheter introducer may be mounted in surrounding relationship to the needle and inserted concurrently with the needle into the selected patient vein. Following such insertion, the needle is retracted by movement of the aforementioned radial locking tab along the axial elongated slot in the main housing to effect the retraction of the needle, thus leaving the short catheter or the catheter introducer, as the case may be, in the desired inserted position within the patient's vein.

When the catheter introducer element is utilized, any desired length of a flexible small diameter catheter may be inserted in the vein and passed through the vein to a position proximate to the body location for which direct application of medication is desired. After such insertion, the catheter introducer element is pulled out of the body and is axially split to effect its removal from the catheter. Such small diameter, flexible catheter may remain in the body for extended periods of time without causing any adverse effects on the patient's vein.

In a preferred embodiment of the invention, the tubular needle mount is formed of a transparent material and the rearward end of the needle mount is closed by a hydrophobic plug or closure. Thus, the initial flow of blood when venipuncture is achieved can be readily visualized by the person performing the catheter introduction procedure by looking through the axially elongated slot.

In another preferred embodiment of the invention, a cylindrical mass of elastomeric material is disposed in closing relationship across the forward end of the bore of the main housing. This mass of material is penetrable by the sharpened end of the needle when the needle is advanced to its forward position for the catheter insertion operation. Upon retraction of the needle, the sharpened end of the needle is positioned within the mass of elastomeric material and hence the opened end of the needle is effectively sealed.

Other advantages of the invention will be readily apparent to those skilled in the art from the following detailed description, taken in conjunction with the annexed sheet drawings, on which is shown several preferred embodiments of the invention.

DESCRIPTION OF PREFERRED EMBODIMENTS

Figure 1:
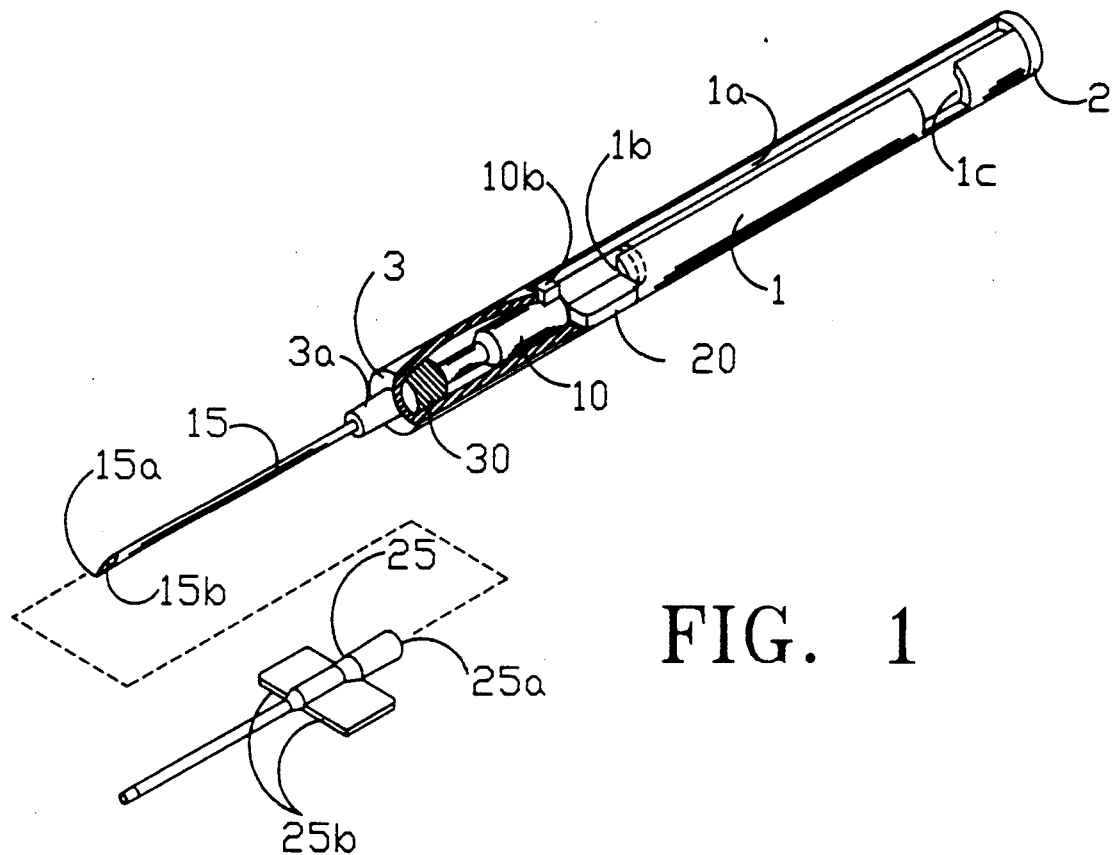
FIG. 1 is an exploded, perspective view of a catheter placement apparatus embodying this invention, and a conventional catheter, showing the hypodermic needle in its forwardly projecting operative position.

Referring to FIG. 1, a catheter placement apparatus embodying this invention comprises a hollow tubular housing 1 having an elongated slot 1a formed in the wall thereof and extending from a position adjacent the forward end of the housing to a position adjacent to the rear end of the tubular housing 1. As used herein, the forward end of the housing 1 is that end which is adjacent to the patient during use. Housing 1 is preferably formed from a readily moldable, yet reasonably rigid plastic material such as polystyrene. A rear end cap 2 of similar material is secured to the open rear end of housing 1 either by an adhesive or by ultrasonic welding. The forward end of tubular housing 1 is closed by an integral annular wall 3 which defines a forwardly projecting tapered male luer connection 3a.

Adjacent the forward and rearward ends of the axially elongated slot 1a, lateral recesses 1b and 1c are respectively provided. As will be later described, these recesses accommodate a locking tab 20 which is mounted for rotational movement with respect to a tubular needle mount 10 which is slidably mounted within the bore of the housing 1.

The forward end of tubular needle mount 10 has a bore 10a configured to snugly receive a conventional hollow hypodermic needle 15 having a sharpened end 15a which exposes the bore 15b of the needle. A radial projection 10b is formed on the medial portion of the tubular needle mount 10 and is in angular alignment with the exposed bore portion 15b of the sharpened end of the needle 15. Radial projection 10b projects into the axially extending elongated slot 1a provided in the housing 1 and maintains the angular position of needle 15 as needle mount 10 is moved from a forward position, wherein the sharpened end of the needle 15 is projecting forwardly relative to the forward end of housing 1, to a rearward position wherein the sharpened end of the needle 15 is entirely retracted to lie within the confines of the housing 1. Obviously, the combined length of the needle 15 and the needle mount 10 is somewhat less than the axial length of the interior of housing 1.

Figure 4:
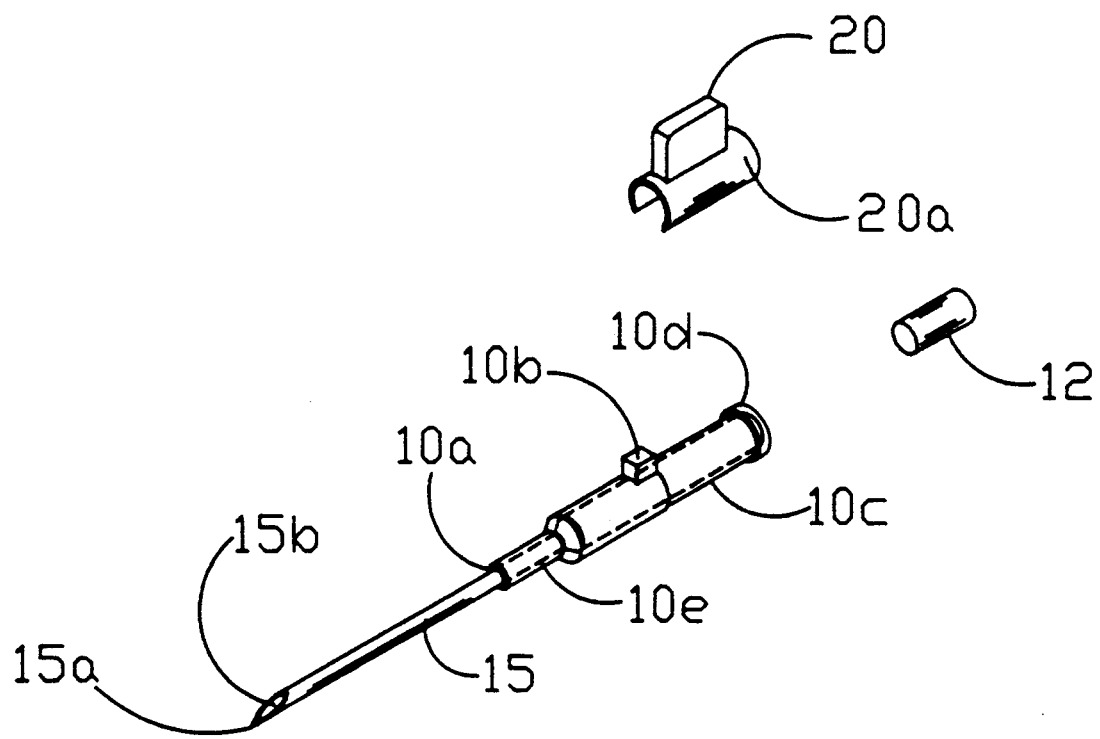
FIG. 4 is an exploded perspective view of FIG. 3.

The needle mount 10 is further provided with a reduced diameter rear portion 10c (FIG. 4) which terminates in an enlarged shoulder 10d. The previously mentioned radial locking tab 20 is rigidly secured to, or integrally formed with, a tubular segment 20a having an arcuate extent slightly greater than 180° to permit such tubular segment to be snapped onto the reduced diameter portion 10c of the needle mount 10, thus securing the locking tab 20 on the needle mount 10, but permitting rotational movement of the locking tab 20 relative to such needle mount. Thus, the operation of the locking tab 20 does not interfere with the alignment of the exposed bore portion 15b of the needle 15 relative to the housing 1.

The needle mount 10 is preferably formed of a transparent extrudable plastic material, such as polystyrene, and its rearward end is closed by a hydrophopic closure 12 which readily permits the passage of air there through but prevents the passage of liquids. Thus, when the needle 15 is inserted in the vein of a patient, the resulting flow of blood passes through the bore 15b of the needle 15 into the bore of the transparent tubular needle mount 10 wherein it is readily visible to the clinician by looking through the elongated slot 1a in the main housing 1, if the main housing 1 is not clearly transparent.

In one application of the apparatus heretofore described, a conventional short catheter 25, which is relatively rigid and has a length sufficient only to insure positive entry into a vein pierced by the needle 16, is secured in position surrounding the needle 15 by an integral female luer connection 25a which is conventionally engagable with the male luer 3a provided on the end of the housing 1. The length of the catheter 25 is proportioned so that the sharpened end 15a of the needle 15 projects slightly out of the forward end of the catheter. Thus, as the needle 15 is inserted into a selected vein of the patient, the catheter is also pushed into the vein. Conventional lateral tabs 25b are provided on the catheter 25 to permit the catheter to be secured by conventional methods to the adjacent body portions of the patient. Once the catheter is thus secured, the needle 15 is retracted from the vein by rotating locking tab 20 and moving the needle mount 10 rearwardly. The housing 1 is rotated to release the luer connection to the catheter 25; and the catheter placement apparatus is removed with the needle safely stored within the interior of the hollow housing 1.

Figure 2:
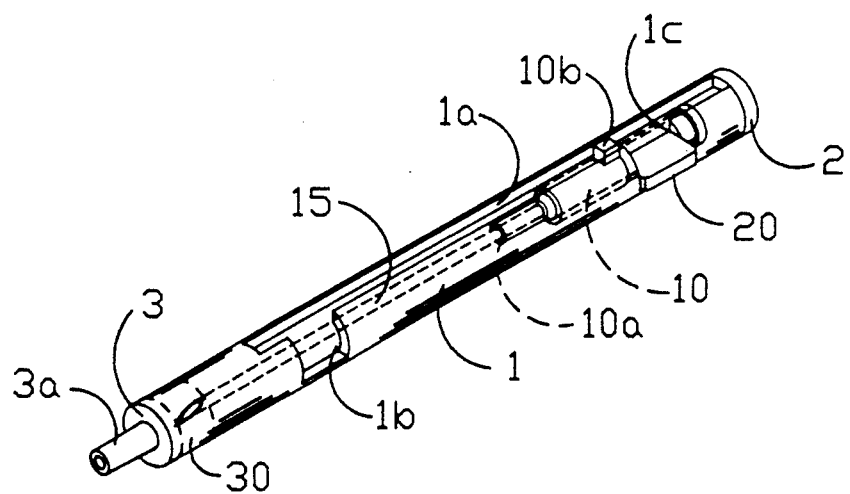
FIG. 2 is a perspective view of the catheter placement apparatus of FIG. 1 with the hypodermic needle in its retracted, inoperative position.
Figure 3:
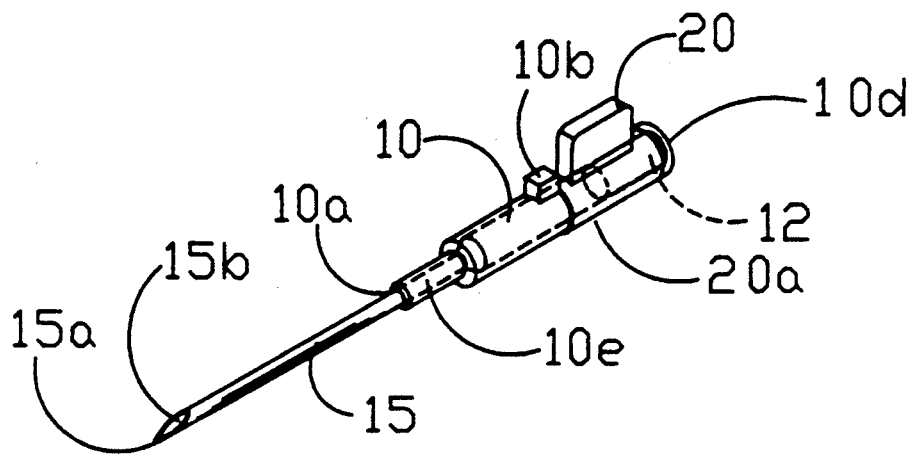
FIG. 3 is a perspective view of the needle mount assemblage utilized in FIG. 1.

In accordance with a preferred embodiment of this invention, and as illustrated in FIG. 2, a cylindrical mass of elastomeric gasket material 30, such as silicone or latex, is mounted in the forward end of the housing 1 immediately adjacent to the annular end wall 3. This elastomeric material is positioned so as to sealingly engage the exposed bore 15b of the needle 15 when the needle 15 and needle mount 10 are retracted to their rearward position wherein the locking tab 20 is in engagement with the rear recess 1c provided on the housing 1. The elastomeric nature of the gasket material causes such material to compress around the opening in the end of the needle 15. Thus, blood (or other body fluids) contained in the tubular needle mount 10 and the hollow needle 15 is prevented from flowing out of the housing 1, and the housing may be safely disposed without presenting any danger of infection to the person doing the disposal.

Figure 5:
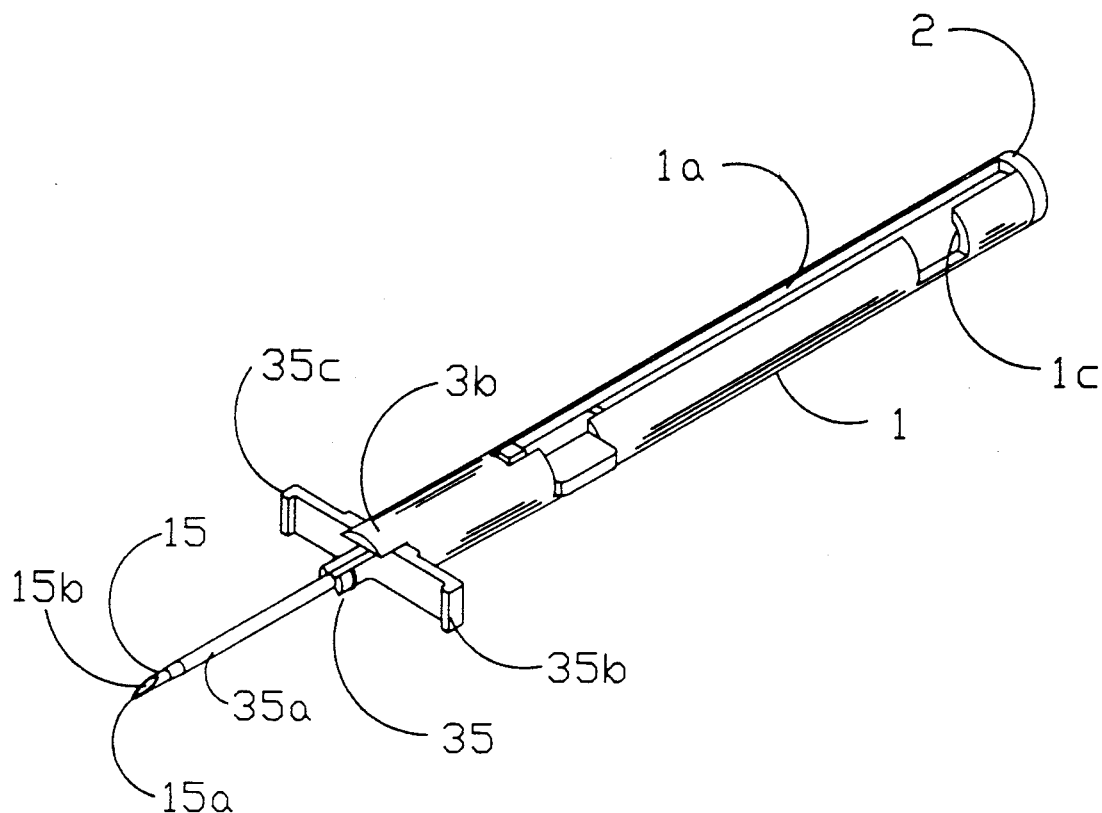
FIG. 5 is a perspective view of an axially splittable catheter guide element assembled on the needle of the catheter introducer apparatus.

In accordance with another modification of this invention, the catheter applicating apparatus may be employed to insert a conventional, axially splittable catheter introducer or guide unit into the selected patient vein. Referring to FIG. 5, the catheter guide unit 35 comprises a small diameter hollow stem portion 35a which is snugly insertable over the needle 15 when the needle is in its projecting position. The rearward end of the catheter guide element is provided with a pair of diametrically opposed handles or grippers 35b and 35c which are normally disposed in abutment with the end wall 3 of housing 1. If desired, end wall 3 may be provided with a forwardly projecting tip 3b to overlie the grippers 35b and 35c. The entire length of the catheter guide unit 35 is provided with two diametrically opposed score lines, which are too small to be shown in the drawings, but are 90° displaced from the manually grippable handles 35b and 35c. A preferred catheter introducer is shown in application Ser. No. 07/922,315 filed Jul. 29, 1992, by George Sinko and Charles Jones.

Figure 6:
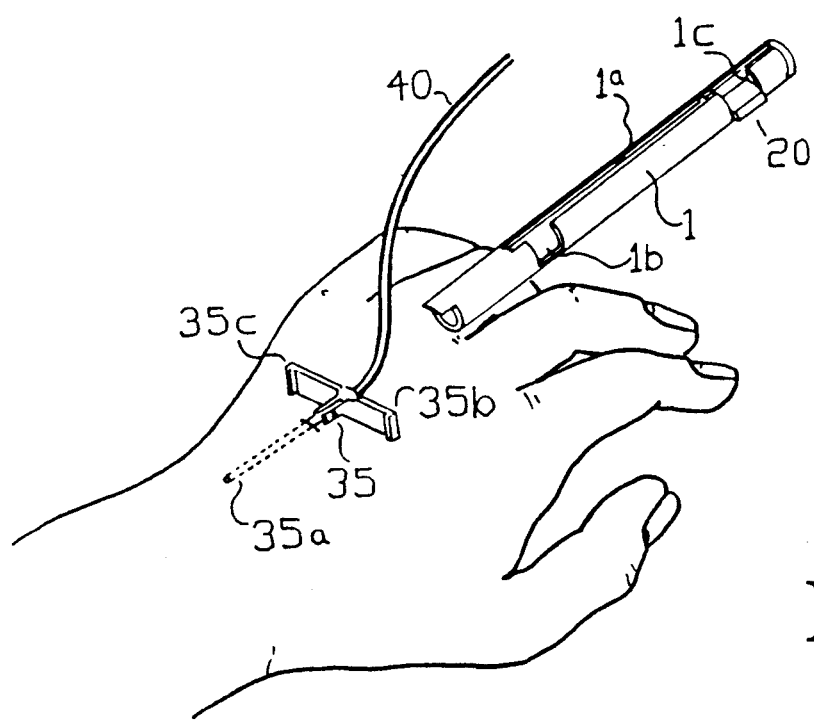
FIG. 6 is a perspective schematic view illustrating the insertion of an axially splittable catheter guide element into a patient's vein and the subsequent insertion of an elongated flexible catheter to selected depth within the vein.

Thus, the catheter guide unit 35 may be inserted into a patient's vein contemporaneously with the piercing of the vein by the sharpened end 15a of the hollow needle 15 (FIG. 6). The needle 15 is then withdrawn back into the body of the housing 1 and locked in such rearward inoperative position by rotating the locking tab 20 to engage the rear recess 1c of the housing 1, as previously described. The housing 1 can then be disengaged from the catheter guide unit 35, leaving the stem portion 35a of such unit in inserted relationship with the selected patient vein.

Then, as best shown in FIG. 6, a selected length of a small diameter flexible catheter 40 may be inserted through the bore of the catheter guide element 35 and run up through the selected vein to a desired position within the vein. When the catheter 40 is thus positioned, the catheter guide unit 35 is removed by first moving it rearwardly relative to catheter 40 to clear the patient's body and then applying a separating force to the two manually graspable gripper portions 35b and 35c to affect the axial splitting of the catheter guide element 35 and its removal from the catheter 40, without in any manner affecting the positioning of the catheter 40.

Figure 7:
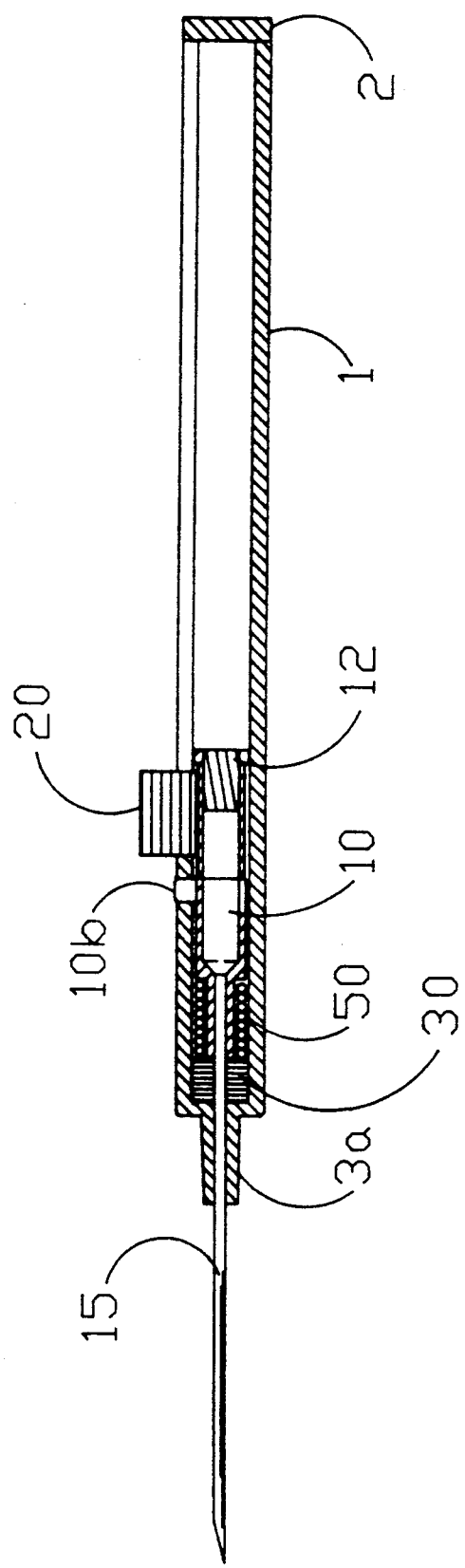
FIG. 7 is a sectional view of a modification of this invention employing a spring to assist in retraction of the hypodermic needle to its inoperative position.

In each of the above described modifications of this invention, a further improvement may be incorporated in the form of a spring which imparts a rearward axial bias to the needle mount 10. As shown in FIG. 7, a spring 50 may be provided which surrounds a reduced diameter, forward end portion 10e of the tubular needle mount 10 and is abuttable against the rearward face of the elastomeric gasket material 30. The spring 50 will obviously be compressed by the forward movement of the needle mount 10 in housing 1 to the operative position of the needle 15, and will be locked against such spring bias by engagement of the locking tab 20 with the forward recess 1b provided in the housing 1. When removal of the applicating apparatus is desired, it is only necessary to flip the locking tab 10 out of the recess 1b with a finger and the spring 50 will effect the automatic retraction of the needle mount 10 to its inoperative position within the housing 1 wherein the sharpened end 15a of the needle 15 is disposed within the elastomeric gasket material 30. As before, the needle can be locked in this inoperative sealed position by rotation of the locking tab 20 into the rearward recess 1c of the housing 1.

From the foregoing description, it is readily apparent to those skilled in the art that this invention provides an inexpensive catheter placement apparatus which may be employed for either introducing a short length, relatively rigid catheter into a patient's vein or alternatively, for introducing a catheter introduction unit into a selected vein and permitting the introduction of a long length, flexible catheter in an advanced position in such vein, following which the catheter introduction unit is axially split to remove it from the catheter. As is well known, small diameter, flexible catheters may be allowed to remain in the patient's body for an extended period because the small diameter and flexibility does not cause rejection by the vein, as is the case with the short length, relatively rigid catheters which should be replaced at least every 48 to 72 hours.

Furthermore, in both applications of the described apparatus, the sharpened end of the needle, as well as the fluid contents of the needle and the flash chamber defined by the tubular needle mount are completely sealed and thus may be disposed of without danger of infection to the personnel doing the disposal operation.

While the utilization of the spring may be desirable in some applications, the needle may be readily retracted by the forefinger of the hand holding the housing 1, thus leaving the other hand completely free to hold the vein inserted catheter or catheter guide element in position during the disconnecting of the placement apparatus from such elements.

Modifications of this invention will be readily apparent to those skilled in the art and it is intended that all such modifications be included within the scope of the appended claims.

I claim:

1. Catheter placement apparatus comprising, in combination:
    a tubular main housing having a bore, a forward end and a rear end;
    an elongated guide slot formed in said main housing and extending from a location adjacent said forward end toward said rear end of said main housing;
    a tubular needle mount slidably mounted in said bore of said main housing for movement from a forward position adjacent said forward end of said main housing to a rearward position adjacent said rear end of said main housing;
    a hollow needle having a sharpened end exposing the bore of said hollow needle;
    means on the forward end of said tubular needle mount for securing said needle thereto with sharpened end disposed in forwardly projecting, coaxial relation to said needle mount;
    a radial projection on said needle mount engaging said guide slot to maintain a fixed radial orientation of said needle end with said main housing;
    the total axial length of said needle and said tubular needle mount being not greater than the axial length of said main housing, whereby movement of said needle mount to said rear end of said main housing will dispose the entire length of said needle within said bore of said main housing; and
    means rotatably mounted on said needle mount for locking said needle mount in either said forward or said rearward position relative to said housing, said locking means being engagable by a finger of the person making the catheter emplacement to move said needle mount between said forward and rearward positions in said main housing.

2. The apparatus of claim 1 further comprising a catheter introduction unit surrounding said needle and insertable in a vein of a patient by entry of the needle into such vein.

3. The apparatus of claim 2 wherein said catheter introduction unit comprises a longitudinally splittable tubular member having a length less than said needle, whereby said sharpened end of said needle projects out of the forward end of said catheter introduction unit to pierce the patient's vein and permit the forward end of the catheter introduction element to enter such vein.

4. The apparatus of claim 3 wherein said tubular catheter introduction unit has a through bore to permit a flexible catheter of any length to be entered into said vein, said catheter introduction unit being longitudinally splittable after introduction of said flexible catheter to a desired position in the patient's vein to remove the catheter introduction unit from the patient's body and said flexible catheter.

5. The apparatus of claim 1 further comprising a catheter surrounding said needle and insertable in a vein of a patient concurrently with the entry of said needle into such vein.

6. The apparatus of claim 1 wherein said means for locking said needle mount in either said forward or said rearward position comprises a pair of lateral recesses respectively formed in the forward and rearward end portions of the wall of said elongated guide slot;

a radial locking tab rotatably mounted on said needle mount; and said locking tab being selectively engagable in one of said recesses by angular movement of said radial locking tab relative to said needle mount.

7. The apparatus of claim 6 wherein said needle mount has a radial shoulder formed thereon in axially spaced relation to said radial projection;

a tubular segment having an arcuate extent slightly greater than 180° snapped on said needle mount intermediate said radial projection and said radial shoulder for rotation relative to said needle mount; and said locking tab being integrally formed on said tubular segment.

8. The apparatus of claim 1, 2, 5, 3, 4 or 6 further comprising a mass of elastomeric material penetrable by said sharpened end of said needle and disposed in the bore of said main housing immediately adjacent said forward end thereof to surround and seal said exposed bore in said sharpened end when said needle mount is shifted to its said rearward position.

9. The apparatus of claim 1, 2, 5, 3, 4 or 6 wherein said needle mount comprises a tubular housing formed of transparent material and defining a flash chamber having one end communicating with the other end of said hollow needle to receive blood issuing from the vein punctured by said sharpened end of the needle; and a hydrophobic closure for the other end of said flash chamber, whereby the flow of blood into said flash chamber may be observed through said guide slot.

10. The apparatus of claim 1, 2, 5, 3, 4 or 6 further comprising resilient means in said housing biasing said needle mount toward said rear end of said housing.

* * * * *